(12) United States Patent
Lokai et al.

(10) Patent No.: US 6,319,983 B1
(45) Date of Patent: Nov. 20, 2001

(54) (METH)ACRYLIC ESTERS CONTAINING URETHANE GROUPS, THEIR PREPARATION, RADIATION-CURABLE COATING COMPOSITIONS AND A PROCESS FOR PREPARING THESE COATING COMPOSITIONS

(75) Inventors: Matthias Lokai, Enkenbach-Alsenborn; Erich Beck, Ladenburg; Wolfgang Reich, Maxdorf; Peter Enenkel, Hessheim; Herbert Marky, Kaiserslautern; Rainer Königer, Freinsheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/539,321

(22) Filed: Mar. 30, 2000

(30) Foreign Application Priority Data

Apr. 1, 1999 (DE) ............................................. 199 15 070

(51) Int. Cl.$^7$ ........................ C09D 175/14; C08G 18/67
(52) U.S. Cl. ............................. 525/28; 525/31; 525/438; 525/440; 525/445; 525/528; 525/532; 528/75
(58) Field of Search ............................. 525/438, 440, 525/445, 28, 31, 528, 532; 528/75

(56) References Cited

U.S. PATENT DOCUMENTS

| 4,192,762 | 3/1980 | Osborn . |
| 5,096,938 | 3/1992 | Beck et al. . |
| 5,684,081 | 11/1997 | Dannhorn et al. . |

FOREIGN PATENT DOCUMENTS

| 3316 592 | 11/1994 | (DE) . |
| 3316 593 | 11/1994 | (DE) . |

*Primary Examiner*—Patricia A. Short
(74) *Attorney, Agent, or Firm*—Oblon, Spivak, McClelland, Maier & Neustadt, P.C.

(57) ABSTRACT

The present invention relates to a process for preparing nondispersing (meth)acrylic esters containing urethane groups, comprising
  a) reacting at least one hydroxyl-containing compound with (meth)acrylic acid in a solvent, to form an ester;
  b) removing the solvent and optionally a part of unreacted (meth) acrylic acid;
  c) reacting the mixture resulting from stage a) or b) with at least one epoxy-functional compound in an amount corresponding to the acid number of the mixture; and
  d) reacting the mixture resulting from stage c) with at least one compound containing isocyanate groups,
and such esters obtainable in this way, and radiation-curable coating compositions comprising said esters, and a process for preparing these coating compositions.

19 Claims, No Drawings

(METH)ACRYLIC ESTERS CONTAINING URETHANE GROUPS, THEIR PREPARATION, RADIATION-CURABLE COATING COMPOSITIONS AND A PROCESS FOR PREPARING THESE COATING COMPOSITIONS

The present invention relates to nondispersing (meth) acrylic esters containing urethane groups, to their preparation and to radiation-curable coating compositions comprising said esters, and a process for preparing these coating compositions.

Radiation-curable binders based on polyesters containing acrylic groups are known. Thermoforming resins of this kind are of great interest owing in particular to their ability to be processed rapidly and with little or even no solvent. The low solvent content of these systems removes the need for laborious, evaporative removal and reprocessing of the solvents. The emissions risks through solvents is substantially reduced. Generally, also important for economic processability, on the part of the binders, besides low raw materials costs and high reactivity, is, in particular, the small amount of very costly reactive diluents that is required in order to establish appropriate processing viscosities.

One possibility to reduce the amount of reactive diluents added, or to do without them entirely, is to use aqueous, radiation-curable binder dispersions.

DE-A-195 25 489, for instance, describes polyester acrylate urethane dispersions based on hydroxyl-containing polyester acrylate prepolymers. These dispersions are prepared by the addition reaction of A) from 40 to 90% by weight of one or more hydroxyl-containing polyester acrylate prepolymers having an OH content of from 40 to 120 mg KOH/g and B) from 0.1 to 20% by weight of one or more mono- and/or difunctional, isocyanate-reactive compounds containing cationic groups, anionic groups and/or groups which have a dispersing action as a result of ether units, together with C) from 10 to 50% by weight of one or more polyisocyanates, followed by reaction with D) from 0.1 to 10% by weight of one or more diamines and/or polyamines.

The cured films obtained from such dispersions are capable of improvement in terms of their mechanical properties, especially as regards a combination of good surface hardness with film flexibility. Furthermore, it is necessary when using these dispersions as coating compositions to take into account the disadvantages associated with the use of water, so that in many cases the use of low-solvent or solvent-free systems is preferred.

Radiation-curable urethane preparations are described in DE 29 15 846. EP-A-0 126 341 and EP-A-0 127 766 describe processes for preparing radiation-curable (meth) acrylic esters by esterifying OH-containing polyesters with excess acrylic or methacrylic acid and then addition-reacting the remaining acrylic or methacrylic acid with diglycidyl or polyglycidyl ethers so as to form nonvolatile 2-hydroxyacrylate esters.

Finally, building on this art, EP-B-0 279 303 describes radiation-curable acrylates obtainable by reacting simultaneously A) 1 equivalent of a dihydric to hexahydric alkoxylated $C_2$–$C_{10}$-alcohol with B) from 0.05 to 1 equivalent of a dibasic to tetrabasic $C_3$–$C_{36}$-carboxylic acid or anhydride thereof, and C) from 0.1 to 1.5 equivalents of acrylic acid and/or methacrylic acid and further reacting the excess carboxyl groups with the equivalent amount of an epoxy compound. Crosslinking of these coating compositions by electron beams or, following the addition of photinitiators, by UV rays gives films which in general conform to the requirements of practice. Nevertheless, in certain cases it can be desirable to improve the hardness, flexibility and/or chemical resistance of the resultant films.

It is an object of the present invention to provide coating compositions based on (meth)acrylic esters which can be used to obtain radiation-cured films of high hardness, good flexibility and sufficient chemical resistance.

We have found that this object is achieved by nondispersing (meth)acrylic esters which contain urethane groups and are obtainable by a) reacting at least one hydroxyl-containing compound with (meth)acrylic acid in a solvent, to form an ester;
b) removing the solvent and optionally a part of unreacted (meth)acrylic acid;
c) reacting the mixture resulting from stage a) or b) with at least one epoxy-functional compound in an amount corresponding to the acid number of the mixture; and
d) reacting the mixture resulting from stage c) with at least one compound containing isocyanate groups.

The (meth)acrylic esters containing urethane groups, according to the invention, are nondispersing; that is, in the absence of further auxiliaries they do not form stable dispersions and/or emulsions. The (meth)acrylic esters containing urethane groups of the invention do not possess dispersing-active groups to a sufficient extent to form stable dispersions and/or emulsions. Dispersing-active groups are, generally, polar functional groups, such as ionogenic and/or ionic groups, especially carboxylic acid groups, sulfonic acid groups, phosphonic acid groups, phosphoric acid groups, alkali metal salts and ammonium salts thereof, quaternary ammonium groups, and ether groups. Hydroxycarboxylic acids, amino acids, aminosulfonic acids, and also polyetherols or $\alpha,\omega$-diaminopolyethers having molecular weights from about 500 to 2000, are commonly used to synthesize dispersing-active polyurethanes, which are then processed in the form of dispersions. The (meth)acrylic esters of the invention, containing urethane groups, are preferably prepared without the abovementioned dispersing-active components; in particular, no dispersing-active groups are incorporated into the (meth)acrylic esters containing urethane groups via the reaction with compounds containing isocyanate groups.

Examples of suitable hydroxyl-containing compounds having two or more hydroxyl groups per molecule are dihydric to hexahydric $C_2$–$C_{20}$-polyols, preferably $C_2$–$C_{10}$-polyols, examples being diols, such as ethylene glycol, 1,2-butanediol, 2-methyl-1,3-propanediol, 1,4-butanediol, 1,5-pentanediol, neopentyl glycol, 1,6-hexanediol, 2-methylpentane-1,5-diol, 2-ethylbutane-1,4-diol, 1,10-decanediol, diethylene glycol, 2,2,4-trimethylpentane-1,5-diol, 2,2-dimethylpropane-1,3-diol, 1,4-dimethylolcyclohexane, 1,6-dimethylolcyclohexane, 1,1'-isopropylenebis(p-phenyleneoxy)di-$\beta$-ethanol, 2,2-bis(4-hydroxyphenyl)propane (bisphenol A); triols, such as glycerol, trimethylolethane, trimethylolpropane, trimethylolbutane; tetraols, such as pentaerythritol, ditrimethylolpropane and hexols, such as erythritol, sorbitol and dipentaerythritol.

Preference is given to trihydric to hexahydric $C_3$–$C_6$-alcohols, such as trimethylolpropane, glycerol, pentaerythritol and sorbitol.

Also suitable are alkoxylation products. For the purposes of the invention, alkoxylation products are the polymerization products obtainable in accordance with conventional techniques by reacting hydroxyl-containing compounds with alkylene oxides or alkylene oxide mixtures, such as ethylene oxide, propylene oxide, tetrahydrofuran and/or butylene oxide. Preference is given to ethoxylation and propoxylation products of the abovementioned polyols. The degree of alkoxylation of these polyetherpolyols is generally between 1 and 30, preferably between 1 and 10.

Preference is given to alkoxylated trimethylolpropane, especially ethoxylated trimethylolpropane.

The abovementioned hydroxyl-containing compounds having two or more hydroxyl groups per molecule have (average) molecular weights in the range from preferably 62 to 4000, in particular from 80 to 800 and, especially, from 90 to 500.

Suitable hydroxyl-containing compounds having one hydroxyl group per molecule are $C_5$–$C_{30}$-monoalcohols, preferably $C_8$–$C_{20}$-monoalcohols, examples being 2-ethylhexanol, lauryl alcohol, stearyl alcohol, 4-t-butylcyclohexanol, 3,3,5-trimethylcyclohexanol, 2-methyl-3-phenylpropan-1-ol and phenylglycol.

Also suitable are corresponding alkoxylation products, preferably ethoxylation and propoxylation products, of $C_2$–$C_{12}$-monoalcohols. The degree of alkoxylation is generally from 1 to 10, preferably from 1 to 5.

The abovementioned hydroxyl-containing compounds having one hydroxyl group per molecule preferably have molecular weights of between 130 and 300.

Further suitable hydroxyl-containing compounds are polyester polyols formed from dihydric to hexahydric $C_2$–$C_{20}$-polyols, with or without alkoxylation, and dibasic to tetrabasic $C_3$–$C_{36}$-carboxylic acids or esterifiable derivatives thereof. Polyester polyols of this kind can be prepared in a separate esterification step and then used in stage a) according to the invention. Alternatively, they can be prepared in situ during the acrylic or methacrylic acid esterification of stage a), by reacting simultaneously in stage a) dihydric to hexahydric $C_2$–$C_{20}$-polyols, with or without alkoxylation, with dibasic to tetrabasic $C_3$–$C_{36}$-carboxylic acids or esterifiable derivatives thereof, and (meth)acrylic acid. Suitable polyols for this purpose are principally the above-described dihydric to hexahydric $C_2$–$C_{10}$-polyols, with or without alkoxylation, and in particular their preferred representatives.

Also suitable in accordance with the invention are polylactone polyols formed from lactones—i.e., cyclic hydroxy-$C_5$–$C_{10}$-alkylcarboxylic acids—having preferably 6- to 8-membered rings, especially caprolactones and in particular ε-caprolactone, and polyols, such as the abovementioned, unalkoxylated or alkoxylated polyols, preference being given to diols and triols. Like the abovementioned polyester polyols, polylactone polyols of this kind can be prepared in accordance with known techniques.

Particularly suitable dibasic to tetrabasic $C_3$–$C_{36}$-carboxylic acids are $C_4$–$C_{15}$-dicarboxylic acids and esterifiable derivatives thereof, such as anhydrides or $C_1$–$C_4$-alkyl esters, examples being succinic acid, succinic anhydride, glutaric acid, glutaric anhydride, adipic acid, pimelic acid, suberic acid, sebacic acid, dodecanedioic acid, phthalic acid, phthalic anhydride, terephthalic acid, isophthalic acid, maleic acid, maleic anhydride, fumaric acid, citraconic acid, tetrahydrophthalic acid, tetrahydrophthalic anhydride, hexahydrophthalic acid, hexachloroendomethylenetetrahydrophthalic acid, dimeric linoleic acid, trimellitic acid, trimellitic anhydride, pyromellitic acid, pyromellitic anhydride, citric acid and tartaric acid, isomers and hydrogenation products of the abovementioned carboxylic acids and esterifiable derivatives thereof, and also mixtures of these. Preference is given to adipic acid, phthalic acid, phthalic anhydride, maleic anhydride and fumaric acid.

Preferred (meth)acrylic esters containing urethane groups are obtainable by using an excess of (meth)acrylic acid in stage a) relative to the hydroxyl groups of the hydroxyl-containing compound(s), preferably in an equivalents ratio of up to 1:1.5 and, in particular, an equivalents ratio of from 1:1.1 to 1:1.25. If polyol, carboxylic acid and (meth)acrylic acid are reacted simultaneously in stage a), then preference is given to equivalents ratios of polyol:carboxylic acid; (meth)acrylic acid of 1:0.05–1:0.1–1.5 and, in particular, of 1:0.1–0.6:0.5–0.9.

The esterification in stage a) takes place preferably in a solvent which forms an azeotropic mixture with water. In this way, the water formed during formation of the ester can be removed azeotropically during the reaction. Advantageous solvents are those which form an azeotrope, especially a minimum azeotrope, with water but not with the other reactants and products. Suitable examples are aliphatic, cycloaliphatic or aromatic hydrocarbons and mixtures thereof. Preference is given to hydrocarbons or hydrocarbon mixtures having a boiling range from 50 to 130° C. and, in particular, between 60 and 110° C. Specific examples are alkanes, such as n-hexane, n-heptane and their isomers and mixtures thereof, cycloalkanes, such as cyclohexane or methylcyclohexane, and aromatic hydrocarbons, such as benzene, toluene, and xylene isomers. Particularly preferred entrainers are heptane, cyclohexane, methylcyclohexane and toluene and also hexane, heptane and isomers thereof, and also mixtures of these having a boiling range of between 60 and 130° C.

Depending on the apparatus used, the amount of hydrocarbon or hydrocarbon mixture added can vary between 0.1 and 2 times the amount of the reaction mixture comprising hydroxyl-containing compound and (meth)acrylic acid. A ratio of reaction mixture to hydrocarbon of from 1:0.20 to 1:0.8 is particularly advantageous.

The temperature imposed during the esterification reaction is preferably chosen such that azeotropic conditions prevail. Under such conditions, the solvent acts as an entrainer to remove the resulting water of reaction. The esterification takes place in general at elevated temperature, generally at from 40 to 130° C., preferably at from 70 to 120° C.

Preferred (meth)acrylic esters containing urethane groups are obtainable by conducting the reaction in stage a) in the presence of at least one polymerization inhibitor. Premature polymerization can generally be avoided by adding small amounts of inhibitor or inhibitors. These can be the usual compounds used to prevent thermal polymerization. Suitable examples are inhibitors based on monohydric and polyhydric phenols, such as p-methoxyphenol, 2,6-di-t-butylphenols, especially 2,6-di-t-butyl-p-cresol, quinones, such as p-benzoquinone, hydroquinones, hydroquinone mono-$C_1$–$C_4$-alkyl ethers, especially hydroquinone monomethyl ether, resorcinol monomethyl ether, thiodiphenylamines, also called phenothiazines, 2,2,6,6-tetramethylpiperidin-1-yloxy, 4-hydroxy-2,2,6,6-tetramethylpiperidin-1-yloxy, phosphorous esters, and tin (II) compounds. Combinations of the above phenol compounds with phenothiazine or tin(II) compounds, and the combination of tin(II) compounds with phenol compounds and phenothiazine, are advantageous. The total amount of polymerization inhibitor is generally from 0.001 to 2.0% by weight, preferably from 0.005 to 0.5% by weight, based on the amount of esterification mixture comprising hydroxyl-containing compound or hydroxyl-containing compounds and (meth)acrylic acid. The phenol-based compounds are used preferably in amounts of from 0.5 to 1% by weight, the tin(II) compounds in amounts of from 0.01 to 1% by weight Sn, and phenothiazine in amounts of from 0.001 to 0.1% by weight, based in each case on the amount of esterification mixture. In general, the abovementioned polymerization inhibitors result in (meth)acrylic esters, containing urethane groups, which have low color numbers. Since colorless products are preferred, the use of suitable additives which reduce product discoloration, such as triphenyl phosphite and hypophosphorous acid, can be of advantage, especially when the temperature stress during the preparation process results in any—albeit only slight—discoloration.

Otherwise, the esterification takes place in accordance with methods which are common knowledge, in the presence of acidic esterification catalysts, such as organic or inorganic acids or acidic ion exchangers, preference being given to sulfuric acid and sulfonic acids, such as p-toluenesulfonic acid and methanesulfonic acid. The acidic esterification catalysts are used generally in amounts of from 0.1 to 3% by weight, based on the esterification mixture.

The esterification is generally continued to a conversion of at least 85%, preferably from 90 to 95%, based on the amount of hydroxyl groups used. The degree of esterification can be determined from the amount of water removed.

The solvent is removed in stage b). This is done preferably by distillation, either following stage a), i.e., after the removal of the water of reaction has ended, or toward the end of stage c); for example, when the acid number of the reaction mixture has dropped to 15 to 5 mg KOH/g. The removal of the solvent may be accompanied by removal of a part of unreacted (meth)acrylic acid. Depending on the amount of (meth)acrylic acid initially employed, on the reaction regime, on the progress of the reaction and/or on the amount of (meth)acrylic acid desired for stage c), it is also possible to carry out deliberate distillative removal of a part of the unreacted (meth)acrylic acid by choosing appropriate distillation conditions. Removal of the solvent and, optionally, of a part of unreacted (meth)acrylic acid preferably takes place by means of vacuum distillation.

In stage b), it is also possible to carry out the preferably complete neutralization of the esterification catalyst with an equivalent amount of a base. The base used can comprise alkali metal bases, such as sodium hydroxide solution, potassium hydroxide solution, sodium carbonate, sodium hydrogen carbonate, potassium carbonate, potassium hydrogen carbonate, and alkaline earth metal bases, such as calcium hydroxide, calcium oxide, magnesium hydroxide or magnesium carbonate, and also ammonia and amines, such as trimethylamine, triethylamine, triisopropylamine etc.

Preferred (meth)acrylic esters containing urethane groups are obtainable by conducting the removal of the solvent and, optionally, of a part of unreacted (meth)acrylic acid in stage b) such that the acid number of the resulting mixture is from 200 to 5 mg KOH/g, preferably from 80 to 15 mg KOH/g. The way in which acid numbers can be determined is known per se.

An essential advantage of the esterification process of the invention is that there is no need for washing operations to remove the esterification catalyst and unreacted (meth)acrylic acid. In this case it is the distillation step which is used to separate off the solvent, a part of unreacted (meth)acrylic acid being removable at the same time if desired.

The mixture resulting from stage b) is then reacted in stage c) with at least one epoxy-functional compound in an amount corresponding to the acid number of the mixture. The acid number is essentially the result of carboxylic acid groups of unreacted (meth)acrylic acid and, if appropriate, other carboxylic acids used in stage a), and/or hydroxyl-containing carboxylic acids which have been produced.

Suitable epoxy-functional compounds include both monoepoxy compounds and polyfunctional epoxides, especially bifunctional or trifunctional epoxides. Examples are epoxidized olefins, glycidyl esters of saturated or unsaturated carboxylic acids, and glycidyl ethers of aliphatic or aromatic polyols. Examples of particularly suitable monoepoxy compounds are versatic acid glycidyl esters and alkyl and aryl glycidyl ethers, such as n-butyl glycidyl ether, 2-ethylhexyl glycidyl ether, phenyl glycidyl ether, o-cresyl glycidyl ether or, preferably, 1,2-epoxybutane. Particularly suitable polyfunctional epoxides are difunctional or trifunctional glycidyl ethers or glycidyl esters. Preference is given to polyglycidyl compounds of the bisphenol A type or glycidyl ethers of polyfunctional alcohols, such as butanediol, glycerol or pentaerythritol. Particular preference is given to bisphenol A diglycidyl ether, an example being Epikote® 828, butanediol diglycidyl ether and pentaerythritol triglycidyl ether.

Preferred (meth)acrylic esters containing urethane groups are obtainable when the epoxy-functional compounds used are monoepoxy compounds when esterifying hydroxyl-containing compounds having only one hydroxyl group per molecule with (meth)acrylic acid and those having at least two epoxide groups per molecule when esterifying hydroxyl-containing compounds having two or more hydroxyl groups per molecule with (meth)acrylic acid.

The reaction in stage c) generally takes place at elevated temperature, preferably at from 80 to 130° C. and, in particular, at from 95 to 115° C. To achieve an effective reaction of carboxyl groups with epoxide groups it can be advantageous to conduct the reaction in the presence of appropriate catalysts. These include in particular tertiary amines, such as tri-$C_1$–$C_4$ amines, an example being tributylamines, an example being tributylamine, quaternary ammonium compounds, such as tetra-$C_1$–$C_4$ alkylammonium halides, an example being tetrabutylammonium bromide, phosphines or Lewis bases, examples being thiodiglycols, especially thiodiglycol itself.

Preferred (meth)acrylic esters containing urethane groups are obtainable by continuing the reaction with epoxy-functional compounds in stage c) until the acid number of the resultant mixture is not more than 10 mg KOH/g, preferably not more than 5 mg KOH/g.

Other preferred (meth)acrylic esters containing urethane groups are obtainable when the mixture resulting from stage c) has a hydroxyl number within the range from 25 to 300 mg KOH/g and, in particular, from 40 to 150 mg KOH/g. The way in which hydroxyl numbers can be determined is known per se.

Furthermore, preferred (meth)acrylic esters containing urethane groups are obtainable if the mixture resulting from stage c) has viscosities of 0.5 to 20 Pas, preferably from 1 to 15 Pas.

The (meth)acrylic ester mixture resulting from stage c) is then reacted in stage d) with at least one compound containing isocyanate groups. Suitable compounds containing isocyanate groups are monoisocyanates and, preferably, polyisocyanates having two or more isocyanate groups per molecule. Preference is given in accordance with the invention to polyisocyanates having from 2 to 5 isocyanate groups per molecule, examples being aliphatic, cycloaliphatic and aromatic di-, tri- and polyisocyanates. Examples of suitable diisocyanates are tetramethylene diisocyanate, hexamethylene diisocyanate and its trimers, 2,3,3-tetramethylhexamethylene diisocyanate, 1,4-cyclohexylene diisocyanate, dicyclohexylmethane diisocyanate, isophorone diisocyanate, 1,4-phenylene diisocyanate, 2,4- and 2,6-tolylene diisocyanate, and isomer mixtures thereof (for example, 80% 2,4 and 20% 2,6 isomer) xylene diisocyanate, tetramethylxylylene diisocyanate, 1,5-naphthylene diisocyanate, 2,4- and 4,4'-diphenylmethane diisocyanate. A suitable triisocyanate is, for example, triphenylmethane 4,4', 4"-triisocyanate. Also suitable are polyisocyanates which are obtainable by addition-reacting the abovementioned isocyanates with polyfunctional compounds containing hydroxyl or amino groups. Also suitable are polyisocyanates formed by allophanate, biuret or isocyanurate formation. These include the isocyanurate of hexamethylene diisocyanate. Also suitable are blocked, reversibly masked polykisisocyanates, such as 1,3,5-tris-[6-(1-methylpropylideneaminoxycarbonylamino)hexyl]-2,4,6-trioxohexahydro-1,3,5-triazine. Particular preference is given to hexamethylene diisocynate and isophorone diisocyanate and mixtures thereof and also to the isocyanurate of hexamethylene diisocyanate.

The molar amounts ratio of isocyanate groups of the compounds containing isocyanate groups that are reacted in stage d) to hydroxyl groups of the mixture resulting from stage c) should be less than 1 and is generally within the range from about 0.1 to 0.75, preferably from about 0.15 to 0.50.

It can be advantageous to accelerate the reaction in stage d) by adding known catalysts for isocyanate addition reactions. Examples that may be mentioned here include triethylamine, 1,4-diazabicyclo[2,2,2]octane, tin dioctoate, and dibutyltin dilaurate.

Particularly preferred (meth)acrylic esters containing urethane groups are obtainable by a) reacting ethoxylated trimethylolpropane and adipic acid with an excess of (meth)acrylic acid in a hydrocarbon which together with water forms an azeotropic mixture, preferably methylcyclohexane, to form an ester;

b) removing the hydrocarbon and a part of unreacted (meth)acrylic acid by distillation, preferably under reduced pressure;

c) reacting the mixture resulting from stage b) with bisphenol A diglycidyl ether in an amount corresponding to the acid number of the mixture; and d) reacting the mixture resulting from stage c) with a mixture of hexamethylene diisocyanate and its isocyanurate.

The present invention provides the processes described above and also nondispersing (meth)acrylic esters containing urethane groups which are obtainable by one of said processes.

The present invention additionally provides for a method for preparing radiation-curable coating compositions comprising these nondispersing (meth)acrylic esters containing urethane groups, in which method said nondispersing (meth) acrylic esters containing urethane groups are mixed with at least one photoinitiator and, if desired, further additives. Such coating compositions are suitable preferably for preparing coatings on, for example, flexible and possibly absorbent substrates, such as wood and wood-based materials, examples being paper and card, and also leather, or on inflexible substrates of metal or plastic. Preferably, they are suitable for producing high-quality, scratchproof and chemical-resistant coating films.

The crosslinking, i.e., curing of the polymers of the invention, can be done with high-energy radiation, such as UV, electrons, X-rays or γ-rays. Of these, UV curing is particularly preferred. It can take place, if desired, in the presence of customary photoinitiators, such as, for example, aromatic ketone compounds, such as benzophenone, alkylbenzophenones, Michler's ketone, anthrone, halogenated benzophenones, 2,4,6-trimethylbenzoyldiphenylphosphine oxide, phenylglyoxylic esters, anthraquinone and its derivatives, benzoin ethers, benzil ketals, hydroxyalkylphenones, acylphosphine oxides or acetophenone derivatives. Mixtures of these compounds can also be used. The amount of photoinitiators used is generally from about 0.01 to 20% by weight, preferably from 0.1 to 10% by weight and, in particular, from 0.5 to 4% by weight, based on the total weight of the components to be cured. Examples of suitable radiation sources are medium-pressure mercury vapor lamps, as described, for Instance, in "UV Curing: Science and Technology" (ed. S. P. Pappas). When curing is carried out using electron beams, acceleration voltages of from 150 to 500 kV are generally used.

For the purpose of processing, the (meth)acrylic esters of the invention, containing urethane groups, can have further reactive diluents, known from the art of radiation curing, added to them if desired. The reactive diluents are generally copolymerizable monomers, such as (meth)acrylic acid alkyl esters or the corresponding esters of maleic, fumaric, tetrahydrophthalic, crotonic, isocrotonic, vinylacetic and itaconic acid. Monomers having more than one double bond per molecule are also suitable, such as the di-, tri- and tetra(meth)acrylates of diols, triols and/or tetraols, and also acrylates of alkoxylated diols and triols, such as ethylene glycol, diethylene glycol, propylene glycol, trimethylene glycol, neopentyl glycol, 1,2-butanediol, 1,3-butanediol, 1,6-hexamethylene glycol, 1,10-decamethylene glycol, trimethylolpropane and pentaerythritol. By way of example, mention will merely be made here of 4-t-butylcyclohexyl acrylate, phenoxyethyl acrylate, hexanediol diacrylate, tripropylene glycol diacrylate and trimethylolpropane triacrylate.

Further additives which may be suitable include synergists, such as amines, thio compounds having α-terminal C—H groups, and ethers; noncocrosslinking solvents, such as aromatic hydrocarbons or esters, such as butyl acetate; extenders, such as talc, heavy spa or silicates; defoamers; levelling agents, and film-forming auxiliaries, such as cellulose derivatives.

The present invention therefore additionally provides radiation-curable coating compositions comprising at least one (meth)acrylic ester of the invention, containing urethane groups, and, in addition, possibly containing photoinitiators and further additives, especially those described above.

The coating compositions of the invention can be applied to the target surfaces by means of spraying, dipping, knife coating, brushing, rolling, flow coating or similar measures. The films are then cured by radiation in a manner known per se.

The cured films obtained in accordance with the invention comply fully with the requirements of practice. In particular, they feature a hardness, flexibility and chemical resistance which is not achieved with the corresponding conventional (meth)acrylic esters.

The present invention is elucidated by means of the following examples, although is not limited thereto.

EXAMPLE 1

Polyester Acrylate Ester Containing Urethane Groups 20.9 kg of ethoxylated trimethylpropane (OH number 610 mg KOH/g), 5.72 kg of adipic acid and 14.1 kg of acrylic acid were added to 17.6 l of methylcyclohexane. Further, 0.2 kg of sulfuric acid, 0.12 kg of hydroquinone monomethyl ether, 0.041 kg of 2,6-di-t-butyl-p-cresol, 0.041 kg of triphenyl phosphite, 0.041 kg of hypophosphorous acid and 0.004 kg of phenothiazine were added. This mixture was heated at reflux and the water of esterification was removed using a Dean-Stark trap. With esterification at an end, the entrainer and a fraction of the excess acrylic acid were removed by distillation under reduced pressure until the acid number was 37.8 mg KOH/g. The reduced pressure was removed and 0.88 kg of tetrabutylammonium bromide and 4.3 kg of Epikote® 828 were added. The reaction mixture was stirred at 107° C. for 5.5 hours until the acid number had fallen to 4.1 mg KOH/g. The product was subsequently cooled to 70° C., and 3.3 kg of Basonat HI 100 were metered in over the course of 10 minutes. The temperature of the reaction mixture was raised to 80° C. and maintained for 4 hours. The resulting reaction mixture was then discharged. The product had a viscosity of 21.2 Pas.

EXAMPLE 2

Conventional Polyester Acrylate Ester

The procedure of Example 1 was followed exactly until the acid number had fallen to 4.1 mg KOH/g. The resulting reaction mixture was cooled to 80° C. and discharged. The product had a viscosity of 3.5 Pas.

EXAMPLE 3

UV Curing 100 parts of acrylic ester containing urethane groups, from Example 1, were mixed with 3 parts of photoinitiator mixture and 8.5 parts of solvent. For comparison purposes, 100 parts of polyester acrylate from Example 2 were mixed with 3 parts of photoinitiator mixture. The components used and certain physical properties of the resulting mixtures are given in Table 1 below:

TABLE 1

| Components | | 1 | 2 | 3 | 4 |
|---|---|---|---|---|---|
| Polyester from Ex. 1 | | 100 | | 100 | |
| Polyester from Ex. 2 | | | 100 | | 100 |
| Irgacure 184 | | 3 | 3 | | |
| Irgacure 500 | | | | 3 | 3 |
| Butyl acetate | | 8.5 | 8.5 | | |
| Physical tests | Conditions | 1 | 2 | 3 | 4 |
| Viscosity Pas | 23° C. | 4 | 4.5 | 4 | 3.2 |
| Reactivity [m/min] | 8 g/m² | 11 | 5 | 23 | 5 |
| Reactivity [m/min] | 50 g/m² | 11 | 5 | 23 | 5 |

Curing was carried out with a lamp from IST at 120 W/cm.

EXAMPLE 4

Testing of the Film Properties

The films obtained in accordance with Example 3 were subjected to a performance test. The results obtained were those given in Table 2:

TABLE 2

| Test conditions | | Physical tests | 1 | 2 | 3 | 4 |
|---|---|---|---|---|---|---|
| 100 | g/m² | Pendulum attenuation [swings] | 35 | 26 | 27 | 22 |
| 25 | g/m² | Erichsen indentation [mm] | 4.8 | 5.1 | 5 | 5 |
| 25 | g/m² | YI (unexposed 1 × 10 m/min) | 3.6 | 3.7 | 3.6 | 3.5 |
| 25 | g/m² | YI (exposed 10 × 10 m/min) | 6 | 5.8 | 9.2 | 7.6 |
| 25 | g/m² | YI (Diff.) | 2.4 | 2.1 | 5.6 | 4.1 |
| 100 | g/m² | Chem. test | 1 | 2 | 6 | 7 |
| 10 | s | Acetone | 0 | 0 | 0 | 0 |
| 5 | h | Red wine | 3 | 3 | 1.5 | 1 |
| 16 | h | Coffee powder | 3 | 3 | 2 | 3 |
| 16 | h | Blackcurrant juice | 3 | 3 | 0.5 | 1 |
| 10 | s | EA-BuAc | 0 | 0 | 0 | 0 |
| 5 | h | Mustard | 3 | 3 | 3 | 3 |
| 16 | h | Lipstick | 2 | 4 | 0 | 4 |
| 10 | min | Mercurochrome | 0 | 0 | 0 | 0 |
| 16 | h | Black ballpoint paste | 4.5 | 4.4 | 4.5 | 4.5 |
| 1 | h | Cleaning products | 0 | 0 | 0 | 0 |

General measurement methods

Viscosities were determined in a Rheomat 30 in accordance with DIN 53019 at a temperature of 23° C. and a shear rate D=250 s$^{-1}$.

Hydroxyl numbers were determined in accordance with DIN ISO 4629.

Acid numbers were determined in accordance with DIN 53402.

Reactivites were determined as follows. The coatings were applied to art printing paper (120 g/m², printed in black over half the sheet) in the stated film thickness using a wire-wound coating bar. The resulting films were radiation-cured on a continuous belt and the belt speed was determined at which the films, after traversing a given stretch of belt, had a scratch-resistant, tack-free surface.

Hardnesses were determined by the pendulum attenuation in accordance with DIN 53157.

Flexibilities were determined by Erichsen indentation in accordance with DIN 53156.

The yellowness index (YI) is a measure of the yellowing and is determined first directly after curing (1×10 m/min) and then after strong exposure (10×10 m/min). The lower the increase in YI caused by the strong exposure, the lower the yellowing.

The chemical resistance was determined in accordance with DIN 68 860 1B. The scores given in Table 2 are based on an assessment scale from 0 to 5, 0 denoting an unattacked film and 5 denoting a completely destroyed film.

We claim:

1. A process for preparing a nondispersing (meth)acrylic ester containing urethane groups, comprising
   a) reacting at least one hydroxyl-containing compound with (meth)acrylic acid in a solvent, to form an ester;
   b) removing the solvent and optionally a part of unreacted (meth)acrylic acid;
   c) reacting the mixture resulting from stage a) or b) with at least one epoxy-functional compound in an amount corresponding to the acid number of the mixture; and
   d) reacting the mixture resulting from stage c) with at least one compound containing isocyanate groups.

2. A process as claimed in claim 1, where stage a) is carried out using at least one hydroxyl-containing compound having two or more hydroxyl groups per molecule, with or without alkoxylation, and/or polyester polyols formed from dihydric to hexahydric $C_2$–$C_{10}$ polyols, with or without alkoxylation, and from dibasic to tetrabasic $C_3$–$C_{36}$ carboxylic acids or esterifiable derivatives thereof.

3. A process as claimed in claim 2, wherein at least one hydroxyl-containing compound having two or more hydroxyl groups per molecule is a dihydric to hexahydric $C_2$–$C_{10}$ polyol.

4. A process as claimed in claim 1, wherein stage a) is carried out by reacting simultaneously dihydric to hexahydric $C_2$–$C_{10}$ polyols, with or without alkoxylation, with dibasic to tetrabasic $C_3$–$C_{36}$ carboxylic acids or esterifiable derivatives thereof, and (meth)acrylic acid.

5. A process as claimed in claim 1, wherein stage a) is carried out using an excess of (meth)acrylic acid relative to the hydroxyl groups of the hydroxyl-containing compound (s).

6. A process as claimed in claim 5, wherein the excess of (meth)acrylic acid relative to the hydroxyl groups of the hydroxyl-containing compound(s) is up to an equivalents ratio of 1:1.5.

7. A process as claimed in claim 5, wherein the excess of (meth)acrylic acid relative to the hydroxyl groups of the hydroxyl-containing compound(s) is an equivalents ratio of from 1:1.5 to 1:1.25.

8. A process as claimed in claim 1, wherein stage a) is carried out using as solvent a hydrocarbon which together with water forms an azeotropic mixture or a hydrocarbon mixture which together with water forms an azeotropic mixture.

9. A process as claimed in claim 8, wherein the solvent is heptane, cyclohexane, methylcyclohexane or toluene, or mixtures thereof.

10. A process as claimed in claim 1, wherein the solvent and, if desired, a part of unreacted (meth)acrylic acid are removed by distillation in stage b).

11. A process as claimed in claim 1, wherein stage c) is carried out using as epoxy-functional compound polyglycidyl ethers or polyglycidyl esters of polyfunctional alcohols.

12. A process as claimed in claim 11, wherein the epoxy-functional compound is bisphenol A diglycidyl ether.

13. A process as claimed in claim 1, wherein the mixture resulting from stage c) has a hydroxyl number within the range from 40 to 150 mg KOH/g.

14. A process as claimed in claim 1, wherein stage d) is carried out using at least one compound containing isocyanate groups, having two or more isocyanate groups per molecule.

15. A process as claimed in claim 14, wherein at least one compound containing isocyanate groups, having two or more isocyanate groups per molecule is hexamethylene diisocyanate, its isocyanurate, isophorone diisocyanate or mixtures thereof.

16. A process as claimed in claim 1, which comprises a) reacting ethoxylated trimethylolpropane and adipic acid with an excess of (meth)acrylic acid in a hydrocarbon which together with water forms an azeotropic mixture, to form an ester;

b) removing the hydrocarbon and a part of unreacted (meth)acrylic acid by distillation;

c) reacting the mixture resulting from stage b) with bisphenol A diglycidyl ether in an amount corresponding to the acid number of the mixture; and d) reacting the mixture resulting from stage c) with the isocyanurate of hexamethylene diisocyanate.

17. A nondispersing (meth)acrylic ester containing urethane groups, obtained by a process as claimed in any one of claims 1 to 16.

18. A radiation curable coating composition comprising at least one nondispersing (meth)acrylic ester containing urethane groups, at least one photoinitiator, and optionally further additives wherein said nondispersing (meth)acrylic ester is prepared by a process comprising a) reacting at least one hydroxyl-containing compound with (meth)acrylic acid in a solvent, to form an ester;

b) removing the solvent and optionally a part of unreacted (meth)acrylic acid;

c) reacting the mixture resulting from stage a) or b) with at least one epoxy-functional compound in an amount corresponding to the acid number of the mixture; and d) reacting the mixture resulting from stage c) with at least one compound containing isocyanate groups, wherein stage c) is carried out using as epoxy-functional compound polyglycidyl ethers or polyglycidyl esters of polyfunctional alcohols.

19. A method for preparing a radiation-curable coating composition, as claimed in claim 18, in which method said nondispersing (meth)acrylic ester containing urethane groups is mixed with at least one photoinitiator and, if desired, further additives.

* * * * *

UNITED STATES PATENT AND TRADEMARK OFFICE
CERTIFICATE OF CORRECTION

PATENT NO. : 6,319,983 B1
DATED : November 20, 2001
INVENTOR(S) : Matthias Lokai et al.

It is certified that error appears in the above-identified patent and that said Letters Patent is hereby corrected as shown below:

Column 9,
Table 1, " "

TABLE 1

| Components | | 1 | 2 | 3 | 4 |
|---|---|---|---|---|---|
| Polyester from Ex. 1 | | 100 | 100 | | |
| Polyester from Ex. 2 | | 100 | 100 | | |
| Irgacure 184 | | 3 | 3 | | |
| Irgacure 500 | | 3 | 3 | | |
| Butyl acetate | | 8.5 | 8.5 | | |
| Physical tests | Conditions | 1 | 2 | 3 | 4 |
| Viscosity Pas | 23° C. | 4 | 4.5 | 4 | 3.2 |
| Reactivity [m/min] | 8 g/m² | 11 | 5 | 23 | 5 |
| Reactivity [m/min] | 50 g/m² | 11 | 5 | 23 | 5 | should read -- --.

TABLE 1

| Components | | 1 | 2 | 3 | 4 |
|---|---|---|---|---|---|
| Polyester from Ex. 1 | | 100 | | 100 | |
| Polyester from Ex. 2 | | | 100 | | 100 |
| Irgacure 184 | | 3 | 3 | | |
| Irgacure 500 | | | | 3 | 3 |
| Butyl acetate | | 8.5 | | 8.5 | |
| Physical tests | Conditions | 1 | 2 | 3 | 4 |
| Viscosity Pas | 23°C | 4 | 4.5 | 4 | 3.2 |
| Reactivity [m/min] | 8 g/m² | 11 | 5 | 23 | 5 |
| Reactivity [m/min] | 50 g/m² | 11 | 5 | 23 | 5 |

Signed and Sealed this

Third Day of September, 2002

Attest:

Attesting Officer

JAMES E. ROGAN
Director of the United States Patent and Trademark Office